(12) United States Patent
Sakagami et al.

(10) Patent No.: US 7,471,984 B2
(45) Date of Patent: Dec. 30, 2008

(54) LOW-FREQUENCY TREATMENT DEVICE

(75) Inventors: Toshimasa Sakagami, Tokyo (JP);
Nobuo Ogiwara, Ageo (JP)

(73) Assignee: Ito Co., Ltd., Tokyo (JP)

( * ) Notice: Subject to any disclaimer, the term of this patent is extended or adjusted under 35 U.S.C. 154(b) by 407 days.

(21) Appl. No.: 11/314,294

(22) Filed: Dec. 21, 2005

(65) Prior Publication Data

US 2007/0142876 A1  Jun. 21, 2007

(51) Int. Cl.
*A61N 1/00* (2006.01)
(52) U.S. Cl. ....................................... 607/48
(58) Field of Classification Search ................. 607/21, 607/48, 70
See application file for complete search history.

(56) References Cited

U.S. PATENT DOCUMENTS

| | | | | |
|---|---|---|---|---|
| 4,960,124 | A | * | 10/1990 | Masaki ........................ 607/70 |
| 4,995,390 | A | * | 2/1991 | Cook et al. .................. 607/21 |

FOREIGN PATENT DOCUMENTS

| | | |
|---|---|---|
| JP | 11-253560 | 9/1999 |
| JP | 2003-010344 | 1/2003 |
| JP | 2004-049651 | 2/2004 |

* cited by examiner

*Primary Examiner*—George Manuel
(74) *Attorney, Agent, or Firm*—Bell, Boyd & Lloyd, LLP

(57) ABSTRACT

A low-frequency treatment device includes electrodes to which a low-frequency pulse signal is supplied so as to apply an electric stimulus to a living body; a section for presetting a number of times of muscle contraction which occurs by applying the electric stimulus; a section for setting a pulse signal conducting time period and a pulse signal pausing time period in an interval; a section for computing a treatment time period based on the number of times of muscle contraction and on the conducting and the pausing time periods; a timer which starts counting a time period when supply of the pulse signal is started, and transmits a stop signal for stopping the supply of the pulse signal when the counted time period reaches the computed treatment time period; and a device for shutting off a circuit for supplying the pulse signal based on the stop signal.

3 Claims, 3 Drawing Sheets

LOW-FREQUENCY TREATMENT DEVICE

BACKGROUND OF THE INVENTION

1. Field of the Invention

The present invention relates to a low-frequency treatment device for medical use, in particular, for applying pulse waves to a living body so as to give an electric stimulus to muscles or the like.

2. Description of the Related Art

Conventionally, low-frequency treatment devices for applying pulse waves to a living body so as to give an electric stimulus to muscles or the like are widely known. In treatment using such a low frequency treatment device, electrodes are attached to a desired part of a living body, and a voltage having a low frequency such as a few Hz to a few hundred Hz is applied to the electrodes, so as to apply an electric stimulus to muscles of the living body. In a known technique, a plurality of pairs of electrodes are attached to a living body, and pulse signals having frequencies which are slightly different from each other are respectively applied to the pairs of electrodes, so as to generate interference waves between the pairs of the electrodes and to equivalently apply a low-frequency voltage to the living body. According to this technique, pulse signals are supplied to the pairs of electrodes from a plurality of oscillators for generating slightly different frequencies, by which low-frequency treatment by interference waves of a few Hz or the like can be easily performed. For example, by using electrodes which oscillate at 4000 Hz and electrodes which oscillate at 4010 Hz, interference waves having a frequency of 10 Hz can be easily generated in a living body (see, for example, Japanese Unexamined Patent Application, First Publication No. 2004-049651, in particular, paragraph Nos. 0018 to 0031, and FIGS. 1 to 5). In addition, the degree of fatigue in muscles may be measured and a low-frequency signal in accordance with the degree of fatigue may be applied to electrodes, thereby effectively stimulating a living body by the electrodes in accordance with the degree of fatigue in muscles (see, for example, Japanese Unexamined Patent Application, First Publication No. H11-253560, in particular, paragraph Nos. 0005 to 0022, and FIGS. 1 to 3). In another known technique, the amplitude of high-frequency carrier waves is modulated using low-frequency waves and the modulated wave signal is applied to electrodes, thereby stimulating from the surface to the deeper parts of a living body by the electrodes (see, for example, Japanese Unexamined Patent Application, First Publication No. 2003-010344, in particular, paragraph Nos. 0018 to 0033, and FIGS. 1 to 5).

In the above conventional low-frequency treatment devices, a time period for treatment can be set in consideration of an objective of treatment. When a preset time period for treatment has elapsed, the value counted by a timer has expired, so that the low-frequency treatment device may automatically stop the operation, or an alarm may ring so as to urge the user to manually stop the treatment device. For example, when the low-frequency treatment device is operated so as to subject a living body to an athletic training regimen with an objective of preventative medicine, the time when the timer has expired can be freely set in accordance with the age, sex, health conditions, or the like of a subject (i.e., a living body) by operating a dial knob provided on an operation face of the low-frequency treatment device. Therefore, when the user sets a desired time period by using the dial knob of the low-frequency treatment device, a voltage (or a current) of a low-frequency pulse signal is supplied to the electrodes only for the set time period, and an electric stimulus can be applied to neuromuscular parts of the living body.

However, when electrodes are attached to a specific part of a living body so as to intermittently apply a low-frequency pulse signal at specific intervals, it is known that the effects of treatment depend not on the treatment time period, but on the number of times of repetition of (a series of) conducting and pausing the pulse signal (i.e., the number of times of muscle contraction (i.e., contractile activity in muscles)). It is also known that determination of the number of times of repetition of conducting and pausing of the pulse signal in accordance with a mode relating to conducting and pausing of the pulse signal, a voltage or a current of the pulse signal, a muscle part to which the electric stimulus is applied, or the like, can produce optimum effects of treatment. However, in the currently-available low-frequency treatment devices, only a time period counted by a timer can be set, and it is impossible to set the most suitable number of times of repetition of conducting and pausing the pulse signal for each subject. Accordingly, the currently-available low-frequency treatment devices cannot produce optimum effects in treatment for each subject, and thus are not convenient.

SUMMARY OF THE INVENTION

In light of the above circumstances, an object of the present invention is to provide a low-frequency treatment device for applying an electric stimulus to neuromuscular parts of a living body by the application of an optimum number of repetitions of a series of conducting and pausing of a pulse signal in accordance with the age, sex, health conditions, a mode relating to conducting and pausing of the pulse signal, a voltage or a current of the pulse signal, or the like.

Therefore, the present invention provides a low-frequency treatment device comprising:

electrodes (e.g., electrodes 4a and 4b in an embodiment explained later) to which a low-frequency pulse signal is supplied so that an electric stimulus is applied to a living body via the electrodes;

a muscle contraction frequency setting section (e.g., a muscle contraction frequency setting section 6 in the embodiment) for presetting a number of times of muscle contraction which occurs by applying the electric stimulus to the living body;

a pulse mode setting section (e.g., a pulse mode setting section 5 in the embodiment) for setting a conducting time period and a pausing time period in an interval, wherein the pulse signal is conducted in the conducting time period and is not conducted in the pausing time period;

a treatment time computing section (e.g., a treatment time computing section 7 in the embodiment) for computing a treatment time period based on the number of times of muscle contraction set by the muscle contraction frequency setting section and on the conducting time period and the pausing time period set by the pulse mode setting section;

a timer (e.g., a timer 9 in the embodiment) which starts counting a time period when supply of the pulse signal is started, and transmits a stop signal for stopping the supply of the pulse signal when the counted time period reaches the treatment time period computed by the treatment time computing section; and a shut-off device (e.g., a switch 8 in the embodiment) for shutting off a circuit for supplying the pulse signal based on the stop signal received from the timer.

According to the above structure, when an optimum number of times of muscle contraction (i.e., an optimum number of times of repetition of (a series of) conducting and pausing a pulse signal) is set in consideration of each objective of treatment, a treatment time period is automatically computed based on a pulse signal conducting and pausing mode (specifically, a conducting time period Ton and a pausing time period Toff in a single interval) which is presently active. When the actual treatment time period reaches the computed value, the power supply of the low-frequency treatment device is automatically shut off, so that no pulses are supplied to the electrodes. According to the present invention, when a mode relating to conducting and pausing of the pulse signal has been determined, it is possible to automatically convert a necessary number of times of muscle contraction (i.e., a number of repetitions of conducting and pausing the pulse signal) to a treatment time period. Therefore, it is unnecessary to count the number of repetitions of conducting and pausing the pulse signal during treatment, and it is possible to perform treatment during the time corresponding to the necessary number of repetitions of conducting and pausing the pulse signal by using a timer which is also provided in conventional devices. Accordingly, it is possible to provide a very convenient low-frequency treatment device.

It is possible that:

the electrodes consist of a first set of electrodes and a second set of the electrodes;

the pulse signal is supplied in one of a selected first pulse supply mode in which the pulse signal is simultaneously supplied to both sets of the electrodes and a selected second pulse supply mode in which the pulse signal is alternately supplied to the first and the second sets of the electrodes;

when the first pulse supply mode is selected, the treatment time computing section computes the treatment time period by:

$$T = N \times (Ton + Toff),$$

where T is the treatment time period, N is the number of times of muscle contraction, Ton is the conducting time period, and Toff is the pausing time period; and when the second pulse supply mode is selected, the treatment time computing section computes the treatment time period by:

$$T = N \times (n \times Ton + Toff),$$

where T is the treatment time period, N is the number of times of muscle contraction, Ton is the conducting time period, Toff is the pausing time period, and n is a rational number other than 1 and is determined according to a predetermined relationship between conducting and pausing of the pulse signal in the second pulse supply mode.

For example, when the first set of electrodes which consists of a pair of electrodes, and the second set of electrodes which also consists of a pair of electrodes are attached to a calf at the back side of a leg, and pulse signals are respectively and simultaneously supplied to the first set of electrodes and the second set of electrodes at a first channel and a second channel after the number N of times of muscle contraction, the conducting time period Ton, and the pausing time period Toff are preset, it is possible to easily convert the necessary number N of times of muscle contraction to the treatment time period T by the formula of "T=N×(Ton+Toff)".

In another example, after the number N of times of muscle contraction, the conducting time period Ton, and the pausing time period Toff are preset, when the first set of electrodes which consists of a pair of electrodes is attached to an anterior tibial muscle at the front side of a leg, and the second set of electrodes which also consists of a pair of electrodes is attached to a calf at the back side of the leg, and the pulse signal is alternately supplied to the first set of electrodes at a first channel and the second set of electrodes at a second channel, it is possible to easily convert the necessary number N of times of muscle contraction to the treatment time period T by the formula of "N×(n×Ton+Toff)", where n is a rational number other than 1 and is determined according to a predetermined relationship between conducting and pausing of the pulse signal in the second pulse supply mode.

Generally, in such a case of alternately supplying the pulse signal to two channels, it is difficult to directly count the number of times of muscle contraction. However, according to the present invention in which the number of times of muscle contraction can be converted to the treatment time period The pulse signal can be reliably supplied for a time period corresponding to the necessary number of muscle contractions.

The present invention also provides a low-frequency treatment device comprising:

electrodes to which a low-frequency pulse signal is supplied so that an electric stimulus is applied to a living body via the electrodes;

a muscle contraction frequency setting section for presetting a number of times of muscle contraction which occurs by applying the electric stimulus to the living body;

a pulse mode setting section for setting a conducting time period and a pausing time period in a single interval, wherein the pulse signal is conducted in the conducting time period and is not conducted in the pausing time period;

a counting device for counting the number of times the electric stimulus is applied from the start of the supply of the pulse signal;

a control section for detecting that the number of times counted by the counting device reaches the number of times of muscle contraction set by the muscle contraction frequency setting section and outputting a stop signal for stopping the supply of the pulse signal; and a shut-off device for shutting off a circuit for supplying the pulse signal based on the stop signal received from the control section.

According to the above structure, when the number of times (i.e., the number of times of outputting the pulse signal) counted by the counting device reaches the number of times of muscle contraction set by the muscle contraction frequency setting section, the power supply of the low-frequency treatment device is automatically shut off, so that no pulses are supplied to the electrodes. Therefore, similarly, it is possible to provide a very convenient low-frequency treatment device.

According to the present invention, when (i) an optimum number of times of muscle contraction is set in consideration of each objective of treatment and (ii) a pulse signal conducting and pausing mode which is most suitable for the objective of treatment are set, a converted treatment time period can be immediately obtained. Therefore, by using a known timer, when the actual number of times of muscle contraction reaches the necessary number of muscle contractions, the supply of the pulse signal can be immediately stopped so as to terminate treatment. Therefore, it is unnecessary to count the number of muscle contractions during the treatment, and a very convenient low-frequency treatment device can be provided.

DETAILED DESCRIPTION OF THE INVENTION

According to a low-frequency treatment device of the present invention, when an optimum number of times of muscle contraction (i.e., an optimum number of times of repetition of (a series of) conducting and pausing a pulse signal) is set, a treatment time period is automatically computed based on a pulse signal conducting and pausing mode which is presently active. When the actual treatment time period reaches the computed value or the number of times of outputting the pulse signal reaches a predetermined value, the power supply of the low-frequency treatment device is automatically shut off. For example, when the optimum number of times of muscle contraction (i.e., the optimum number of times of repetition of conducting and pausing the pulse signal) is set to 25 times, and conducting and pausing time periods in the presently-active pulse signal conducting and pausing mode are respectively set to 4 seconds and 6 seconds, the treatment time period is computed by "10 sec×25 times=250 sec", that is, the treatment time period is 4 minutes and 10 seconds. Accordingly, when a time period of 4 minutes and 10 seconds has elapsed from the start of supply of the pulse signal (i.e., the start of treatment), the power supply of the low-frequency treatment device is automatically shut off. Therefore, an electric stimulus can be applied to a target muscle for the desired number of times (i.e., 25 times) of repetition of conducting and pausing of the pulse signal, that is, the optimum number of times (i.e., 25 times) of muscle contraction. According to the present invention, when a mode relating to conducting and pausing of the pulse signal has been determined, it is possible to automatically convert a necessary number of repetitions of conducting and pausing the pulse signal to a treatment time period. Therefore, it is unnecessary to count the number of repetitions of conducting and pausing the pulse signal during treatment, and it is possible to perform treatment during the time corresponding to the necessary number of repetitions of conducting and pausing the pulse signal by using a timer which is also provided in conventional devices.

Hereinafter, an embodiment of a low-frequency treatment device according to the present invention will be described with reference to the appended figures.

Figure 1:
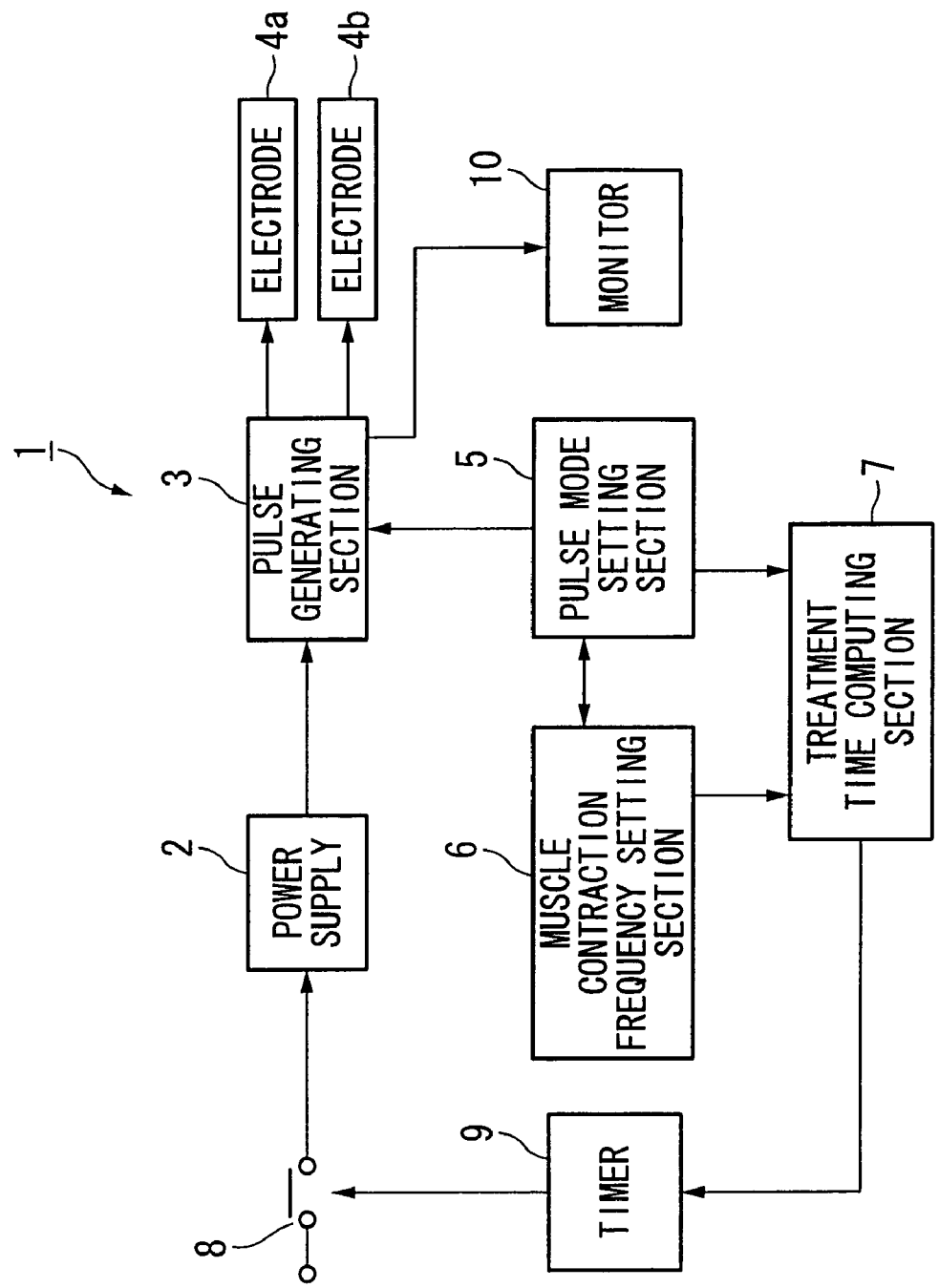
FIG. 1 is a block diagram showing the structure of a low-frequency treatment device as an embodiment according to the present invention.

FIG. 1 is a block diagram showing the structure of a low-frequency treatment device 1 of the embodiment. In FIG. 1, the low-frequency treatment device 1 has (i) a power supply 2 consisting of electric cells or the like, (ii) a pulse generating section 3 for generating a low-frequency pulse signal, for example, having a frequency of 40 Hz, (iii) a pair of electrodes 4a and 4b for receiving the pulse signal from the pulse generating section 3 and applying an electric stimulus to a living body, (iv) a pulse mode setting section 5 for setting a pulse mode relating to an electric current of the pulse signal, time periods for conducting and pausing the pulse signal (i.e., a conducting time period and a pausing time period), and the like, (v) a muscle contraction frequency setting section 6 for setting the number of times of muscle contraction necessary for treatment (i.e., the optimum number of repetitions of a series of conducting and pausing the pulse signal), (vi) a treatment time computing section 7 for computing a time period for treatment based on the time periods of conducting and pausing of the pulse signal, set by the pulse mode setting section 5, and the number of times of muscle contraction set by the muscle contraction frequency setting section 6, (vii) a timer 9 for transmitting a stop signal to a switch 8 of the power supply 2 when the time period set by the treatment time computing section 7 has elapsed, (viii) the switch 8 for shutting off the circuit of the power supply 2 based on the stop signal sent from the timer 9 and stopping the operation of the low-frequency treatment device 1, and (ix) a monitor 10 for monitoring the waveform or the current of the pulse signal output from the pulse generating section 3.

In addition, in accordance with the pausing time period of the pulse signal set by the pulse mode setting section 5, the pulse generating section 3 can temporarily halt the supply of the pulse signal to the electrodes 4a and 4b.

The following items can be set by the pulse mode setting section 5: (i) a name of a target muscle for treatment (e.g., a quadriceps femoris muscle, an anterior tibial muscle, a calf muscle, an arm flexor muscle, a back extensor/contractor muscle, or a shoulder deltoid muscle), (ii) the frequency of the pulse signal (e.g., 10 Hz, 25 Hz, or 40 Hz), (iii) the current of the pulse signal (e.g., 45 mA, 60 mA, or 85 mA), (iv) a type of electrodes (e.g., a carbon deposit rubber plate (Rc) or a metal plate (Mp)), (v) a combination type of electrodes (e.g., a single electrode, a pair of electrodes, two pairs of electrodes, a plurality of pairs of electrodes), and (vi) a conducting time period and a pausing time period (e.g., 4-sec conducting and 6-sec pausing, or 5-sec conducting and 5-sec pausing). In addition, in the muscle contraction frequency setting section 6, another item (vii), namely the number of times of muscle contraction (e.g., 10 times, 20 times, or 25 times) for each kind of training, can be set. All or some of the above seven items can be set according to necessity, although at least the items (vi) and (vii) must be set, that is, the conducting time period and the pausing time period must be set by the pulse mode setting section 5, and the number of times of muscle contraction for each kind of training must be set by the muscle contraction frequency setting section 6.

The electrodes 4a and 4b are attached to a desired muscle part of a living body. A pair of the electrodes 4a and 4b may be attached, or two or more pairs of the electrodes 4a and 4b may be attached. When two or more pairs of the electrodes 4a and 4b are used, such a plurality of electrodes may be connected in parallel to the pulse generating section 3 in FIG. 1 so as to apply the same pulse signal to all electrodes. In another example (not shown), two pairs of electrodes may be arranged perpendicularly to each other on a surface of a target muscle, and pulse signals having slightly different frequencies are respectively applied to the pairs, thereby generating interference between the frequencies. In addition, only a single electrode 4a or 4b may be used.

Below, the operation of the low-frequency treatment device 1 having the structure shown in FIG. 1 will be explained. When a user attaches the electrodes 4a and 4b to a desired part and turns the switch 8 on, the low-frequency treatment device 1 enters a standby mode in which various setting operations can be performed. In the standby mode, a number N of muscle contractions most suitable for the objective of treatment is first set by using the muscle contraction frequency setting section 6. Here, the value of the number N of muscle contractions most suitable for each objective of treatment is predetermined in a table, for each muscle part to be stimulated, or each objective for treatment. Therefore, the user can select a desired value of the number N of muscle contractions by referring to the table.

In addition, a conducting time period Ton and a pausing time period Toff in a single interval are set, which belong to the minimum set items. The treatment time computing section 7 then automatically computes a necessary treatment time period T based on the number N of muscle contractions set by the muscle contraction frequency setting section 6 and the conducting time period Ton and the pausing time period Toff which are set by the pulse mode setting section 5. That is, the treatment time computing section 7 computes the treatment time period T corresponding to the desired number N of muscle contractions, by a formula of "T=(Ton+Toff)×N".

After the above setting operation is completed, the user again pushes on the switch 8, so that the pulse generating section 3 generates a pulse signal which is supplied to the electrodes 4a and 4b. In this operation, the pulse generating section 3 alternately repeats conducting and pausing of the pulse signal based on a pulse mode set by the pulse mode setting section 5, that is, on the conducting time period Ton and the pausing time period Toff. For example, if the pulse signal is supplied while "4-sec conducting and 6-sec pausing" is set by the pulse mode setting section 5, a target muscle is stimulated via the electrodes 4a and 4b by an interval determined by "4-sec conducting and 6-sec pausing", so that a desired electric stimulus can be applied to the muscle to which the electrodes 4a and 4b are attached.

The timer 9 starts time counting simultaneously when the supply of the pulse signal is started. When the treatment time period T (set by the treatment time computing section 7 based on the number N of muscle contractions, the conducting time period Ton, and the pausing time period Toff) has elapsed, the timer 9 transmits a stop signal to the switch 8 so as to shut off the switch 8.

More specifically, the operation of stopping the pulse signal can be performed as explained below. In an example, when the treatment time period T is computed by the treatment time computing section 7, data of the treatment time period T is immediately transmitted to the timer 9 and stored in a memory (not shown) of the timer 9. The timer 9 always compares the elapsed time of the supply of the pulse signal (or the number of times of outputting the pulse signal) with the treatment time period T (or a preset number of times of outputting the pulse signal), and when the elapsed time (or the number of times of outputting the pulse signal) reaches the treatment time period (or the preset number of times of outputting the pulse signal), the timer 9 transmits a stop signal to the switch 8. During the operation, the waveform, the current, the mode of conducting and pausing time periods, or the like, can always be monitored by a screen of the monitor 10.

In addition, if a muscle portion, a frequency or a current of a pulse signal, a kind and a combination type of the electrodes, or the like, are designated or set by the pulse mode setting section 5 before setting the conducting time period and the pausing time period, a conducting time period and a pausing time period which are most suitable for the current mode are automatically displayed, and the shown conducting time period and pausing time period may be set. Such an operation will be explained in further detail in specific examples explained later.

Figure 2A:
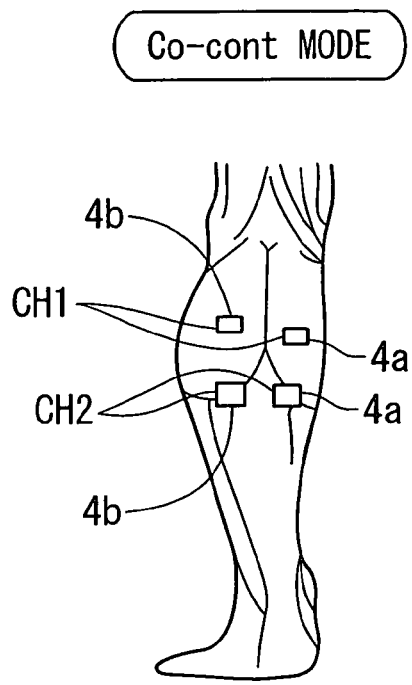
FIG. 2A is a general view showing a state in which electrodes are attached to a calf of a leg.
Figure 2B:
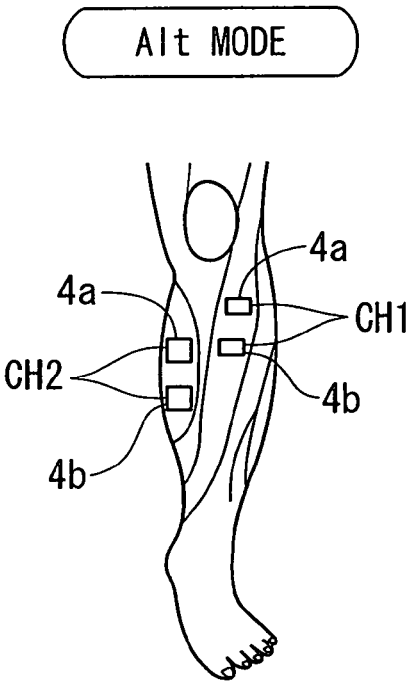
FIG. 2B is a general view showing a state in which electrodes are attached to an anterior tibial muscle and a calf of a leg.

Below, the operation of the low-frequency treatment device 1 will be explained based on specific examples. FIGS. 2A and 2B are general views showing different states, in each of which electrodes are attached to a leg. In FIG. 2A, the electrodes are attached to a calf, while in FIG. 2B, the electrodes are attached to an anterior tibial muscle and a calf. More specifically, in the case of FIG. 2A, two pairs of electrodes 4a and 4b are attached to a calf at the back side of a leg, and pulse signals are simultaneously supplied to the two pairs at two channels (CH1 and CH2). This mode is called a "Co-cont mode", below.

In the case of FIG. 2B, a pair of the electrodes 4a and 4b is attached to an anterior tibial muscle at the front side of a leg so as to supply a pulse signal at a channel (CH1), and another pair of the electrodes 4a and 4b is attached to a calf at the back side of the leg so as to supply a pulse signal at another channel (CH2). In this case, the pulse signal is alternately conducted between the two channels (CH1 and CH2). This mode is called an "Alt mode" below.

Figure 3:
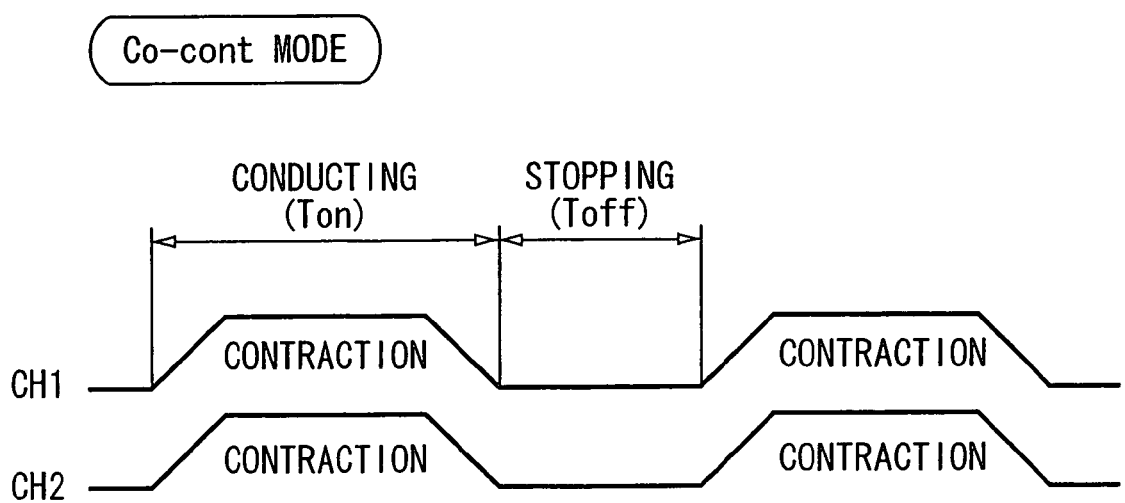
FIG. 3 shows waveforms of conducting and pausing of the pulse signals in the Co-cont mode shown in FIG. 2A.

FIG. 3 shows waveforms of conducting and pausing of the pulse signals in the Co-cont mode shown in FIG. 2A. In FIG. 3, the horizontal axis shows the elapsed time, and FIG. 3 shows the state in which pulse signals are simultaneously supplied to the two pairs of the electrodes at the two channels CH1 and CH2. That is, when the two pairs of the electrodes 4A and 4B are attached to a calf as shown in FIG. 2A and conducting and pausing of pulse signals are simultaneously repeated at the two channels CH1 and CH2, muscle contraction repeatedly occurs in each conducting time period Ton, while muscle contraction stops in the pausing time period Toff, as shown in FIG. 3.

Therefore, when the pulse mode relating to the conducting time period Ton and the pausing time period Toff as shown in FIG. 3 is set by the pulse mode setting section 5 and the number N of muscle contractions is set by the muscle contraction frequency setting section 6, the treatment time setting section 7 computes the treatment time period T by the following formula (1):

$$T = N \times (T\text{on} + T\text{off}) \tag{1}$$

where N indicates the number of times of muscle contraction, Ton indicates the conducting time period, and Toff indicates the pausing time period.

When the elapsed time reaches the treatment time period T computed by the above formula (1), the timer 9 shuts off the switch 8. Therefore, when the number of times of muscle contraction in the operation reaches the desired number N of muscle contractions set by the user, the low-frequency treatment device 1 can be automatically stopped so as to stop the treatment.

Figure 4:
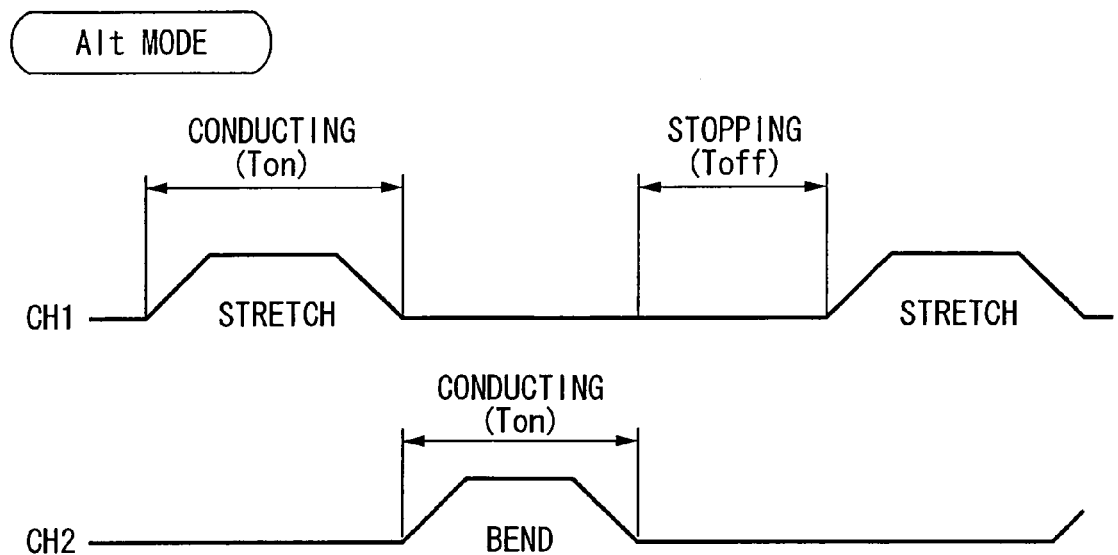
FIG. 4 shows waveforms of conducting and pausing of the pulse signals while the channels CH1 and CH2 are alternately conducted in the Alt mode shown in FIG. 2B.

FIG. 4 shows waveforms of conducting and pausing of the pulse signals while the channels CH1 and CH2 are alternately conducted in the Alt mode. More specifically, FIG. 4 shows a state in which alternate conducting of the channels CH1 and CH2 and pausing of the pulse signal are repeated in a manner such that the pulse signal is first supplied in the channel CH1 to a pair of the electrodes 4a and 4b attached to the anterior tibial muscle at the front side of a leg, and next the pulse signal is supplied in the channel CH2 to another pair of the electrodes 4a and 4b attached to the calf at the back side of the leg, and then no pulse signals are supplied to the electrodes 4a and 4b. In FIG. 4, the horizontal axis also shows the elapsed time.

As shown in FIG. 4, (i) during the conducting time period Ton at the channel CH1, an electric stimulus is supplied to the anterior tibial muscle at the front side of the leg, thereby activating a stretching exercise of the leg, (ii) during the conducting time period Ton at the channel CH2, an electric stimulus is supplied to the calf at the back side of the leg, thereby activating a bending motion of the leg, and (iii) during the pausing time period Toff, no electric stimulus is applied and no kinetic motion is activated. The above three modes are repeatedly performed.

Therefore, when the pulse mode relating to the conducting time period Ton for the channel CH1, the conducting time period Ton for the channel CH2, and the pausing time period Toff, as shown in FIG. 4, are set by the pulse mode setting section 5 and the number N of muscle contractions is set by the muscle contraction frequency setting section 6, the treatment time setting section 7 computes the treatment time period T by the following formula (2):

$$T = N \times (2Ton + Toff) \quad (2)$$

where N indicates the number of times of muscle contraction, Ton indicates the conducting time period, and Toff indicates the pausing time period.

When the elapsed time reaches the treatment time period T computed by the above formula (2), the timer 9 shuts off the switch 8. Therefore, when the number of times of muscle contraction in the operation reaches the desired number N of muscle contractions set by the user, the low-frequency treatment device 1 can be automatically stopped so as to stop the treatment.

Figure 5:
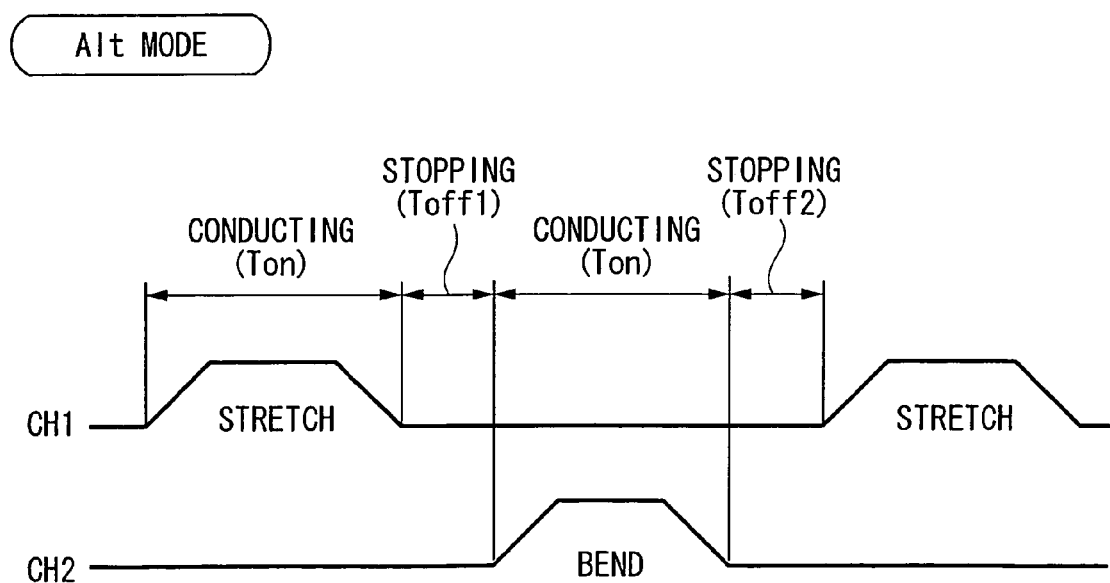
FIG. 5 shows a variation of the waveforms of conducting and pausing of the pulse signals shown in FIG. 4.

FIG. 5 shows another example of supply of the pulse signals, in which two pausing time periods Toff exist on either side of the conducting time Ton in the channel CH2. In this case, the treatment time period T can be computed by the following formula (3):

$$T = N \times (2Ton + Toff1 + Toff2) \quad (3)$$

Below, concrete examples of set conditions for treatment using the low-frequency treatment device 1 will be explained. By employing the following set conditions, the number of times of muscle contraction is converted to the treatment time period, so that an electric stimulus can be applied to each muscle part of a living body, with an optimum number of repetitions of conducting and pausing of the pulse signals.

CONCRETE EXAMPLE 1

(i) the name of a target muscle: the quadriceps femoris muscle, (ii) the frequency of the pulse signal: 50 Hz, (iii) the current of the pulse signal: 85 mA, (iv) the type of electrodes: the carbon deposit rubber plate (Rc), (v) the combination type of electrodes: two pairs of electrodes (type: Q), (vi) the conducting time period and the pausing time period: 10-sec conducting and 50-sec pausing, and (vii) the number of times of muscle contraction: 10 times.

CONCRETE EXAMPLE 2

(i) the name of a target muscle: the anterior tibial muscle, (ii) the frequency of the pulse signal: 60 Hz, (iii) the current of the pulse. signal: 45 mA, (iv) the type of electrodes: Rc, (v) the combination type of electrodes: a single electrode (type: M), (vi) the conducting time period and the pausing time period: 8-sec conducting and 24-sec pausing, and (vii) the number of times of muscle contraction: 12 times.

CONCRETE EXAMPLE 3

(i) the name of a target muscle: the arm flexor muscle, (ii) the frequency of the pulse signal: 40 Hz, (iii) the current of the pulse signal: 60 mA, (iv) the type of electrodes: a metal plate (Mp), (v) the combination type of electrodes: a pair of electrodes (type: B), (vi) the conducting time period and the pausing time period: 4-sec conducting and 12-sec pausing, and (vii) the number of times of muscle contraction: 8 times.

CONCRETE EXAMPLE 4

(i) the name of a target muscle: the back extensor/contractor muscle, (ii) the frequency of the pulse signal: 35 Hz, (iii) the current of the pulse signal: 90 mA, (iv) the type of electrodes: Rc, (v) the combination type of electrodes: a plurality of pairs of electrodes (type: Mu), (vi) the conducting time period and the pausing time period: 6-sec conducting and 30-sec pausing, and (vii) the number of times of muscle contraction: 12 times.

As shown in the above concrete examples, when the name of a target muscle, the frequency of the pulse signal, the current of the pulse signal, the type of electrodes, and the combination type of electrodes are input by using the pulse mode setting section 5, the conducting time period and the pausing time period which are most suitable for the set mode are determined. Therefore, when the number of times of muscle contraction in the mode is successively set, the number of times of muscle contraction is converted to a treatment time period.

As explained above, according to the low-frequency treatment device of the present invention, when a user attaches electrodes to a desired portion of a living body so as to apply an electric stimulus to muscles, the user may set the number of times of muscle contraction determined for each objective of treatment, the name of a target muscle, the frequency of the pulse signal, the current of the pulse signal, the type of electrodes, the combination type of electrodes, and the conducting and the pausing time periods of the pulse signal, thereby automatically computing an optimum treatment time period and performing the supply of the pulse signal only during the treatment time period. Therefore, it is possible to effectively apply an electric stimulus to the target muscle. Accordingly, treatment can be performed with the optimum number of muscle stimuli suitable for each objective of treatment, for example, an objective to train a weakened muscle and perform a balance training for preventing a fall, or an objective of performing a rehabilitation exercise effective for disease treatment.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

For example, setting of muscle contraction is not limited to direct input of a numeric value. In a variation, when a treatment time period is set, the time period is converted to a corresponding number of times and the number of times is displayed together with the treatment time period. After that, the shown number of times may be corrected according to necessity, and the determined number of times is set using a setting switch or the like.

What is claimed is:

1. A low-frequency treatment device comprising:
   electrodes to which a low-frequency pulse signal is supplied so that an electric stimulus is applied to a living body via the electrodes;
   a muscle contraction frequency setting section for presetting a number of times of muscle contraction which occurs by applying the electric stimulus to the living body;
   a pulse mode setting section for setting a conducting time period and a pausing time period in an interval, wherein the pulse signal is conducted in the conducting time period and is not conducted in the pausing time period;

a treatment time computing section for computing a treatment time period based on the number of times of muscle contraction set by the muscle contraction frequency setting section and on the conducting time period and the pausing time period set by the pulse mode setting section;

a timer which starts counting a time period when supply of the pulse signal is started, and transmits a stop signal for stopping the supply of the pulse signal when the counted time period reaches the treatment time period computed by the treatment time computing section; and a shut-off device for shutting off a circuit for supplying the pulse signal based on the stop signal received from the timer.

2. A low-frequency treatment device comprising:

electrodes to which a low-frequency pulse signal is supplied so that an electric stimulus is applied to a living body via the electrodes;

a muscle contraction frequency setting section for presetting a number of times of muscle contraction which occurs by applying the electric stimulus to the living body;

a pulse mode setting section for setting a conducting time period and a pausing time period in a single interval, wherein the pulse signal is conducted in the conducting time period and is not conducted in the pausing time period;

a counting device for counting the number of times the electric stimulus is applied from the start of the supply of the pulse signal;

a control section for detecting that the number of times counted by the counting device reaches the number of times of muscle contraction set by the muscle contraction frequency setting section and outputting a stop signal for stopping the supply of the pulse signal; and a shut-off device for shutting off a circuit for supplying the pulse signal based on the stop signal received from the control section.

3. The low-frequency treatment device according to claim 1, wherein:

the electrodes consist of a first set of electrodes and a second set of the electrodes;

the pulse signal is supplied in one of a selected first pulse supply mode in which the pulse signal is simultaneously supplied to both sets of the electrodes and a selected second pulse supply mode in which the pulse signal is alternately supplied to the first and the second sets of the electrodes;

when the first pulse supply mode is selected, the treatment time computing section computes the treatment time period by:

$$T = N \times (T\text{on} + T\text{off}),$$

where T is the treatment time period, N is the number of times of muscle contraction, Ton is the conducting time period, and Toff is the pausing time period; and when the second pulse supply mode is selected, the treatment time computing section computes the treatment time period by:

$$T = N \times (n \times T\text{on} + T\text{off}),$$

where T is the treatment time period, N is the number of times of muscle contraction, Ton is the conducting time period, Toff is the pausing time period, and n is a rational number other than 1 and is determined according to a predetermined relationship between conducting and pausing of the pulse signal in the second pulse supply mode.

* * * * *